US012657835B2

(12) United States Patent
Golenberg et al.

(10) Patent No.: US 12,657,835 B2
(45) Date of Patent: Jun. 16, 2026

(54) EXTENDED REALITY TRAINING PLATFORM

(71) Applicant: COVIDIEN LP, Mansfield, MA (US)

(72) Inventors: Lavie P. Golenberg, Singapore (SG); Kwee Yin Tan, Singapore (SG); Hin Chun Lee, Singapore (SG); Wai Leng Yan, Singapore (SG); Melvin Sim, Singapore (SG); Saravana Kumar Duraiswamy Jalasundaram, Singapore (SG); Chin Mian Tan, Singapore (SG)

(73) Assignee: Covidien LP, Mansfield, MA (US)

( * ) Notice: Subject to any disclaimer, the term of this patent is extended or adjusted under 35 U.S.C. 154(b) by 283 days.

(21) Appl. No.: 18/224,896

(22) Filed: Jul. 21, 2023

(65) Prior Publication Data
US 2024/0029367 A1      Jan. 25, 2024

(30) Foreign Application Priority Data

Jul. 22, 2022      (SG) ............................ 10202250543G

(51) Int. Cl.
*G06T 19/00*          (2011.01)
*G02B 27/01*          (2006.01)
                          (Continued)

(52) U.S. Cl.
CPC .......... *G06T 19/006* (2013.01); *G02B 27/017* (2013.01); *G06F 3/011* (2013.01);
                          (Continued)

(58) Field of Classification Search
None
See application file for complete search history.

(56) References Cited

U.S. PATENT DOCUMENTS 11,663,929 B2 *    5/2023    Okayama ............. G09B 23/303
                                                              434/268
2013/0006036 A1 *    1/2013    Raleigh ................ A61N 5/1077
                                                              382/128
                          (Continued)

FOREIGN PATENT DOCUMENTS

WO          2011127379 A2      10/2011
WO          2017151963 A1      9/2017
                          (Continued)

OTHER PUBLICATIONS

Extended European Search Report for Application No. 23187353.0-1218; Date of Mailing: Nov. 27, 2023; 14 pages.

*Primary Examiner* — Jwalant Amin

(57)          ABSTRACT

Examples described herein provide a method including determining a model location of a physical model by an augmented reality (AR) control application; operating the AR control application to display a holographic body overlaying the physical model via a display device, wherein the holographic body is aligned with the physical model such that a portion of the physical model representing an anatomical structure appears aligned with the holographic body in a predetermined anatomical position; maintaining alignment of the holographic body overlaying the physical model on the display device in real-time while a user interacts with the physical model using a physical medical instrument to simulate a predetermined procedure; and providing haptic feedback to the user during the predetermined procedure.

17 Claims, 14 Drawing Sheets

(51) Int. Cl.

| | |
|---|---|
| *G06F 3/01* | (2006.01) |
| *G09B 23/28* | (2006.01) |
| *G16H 30/40* | (2018.01) |
| *A61B 34/00* | (2016.01) |
| *A61N 1/372* | (2006.01) |
| *G06V 30/224* | (2022.01) |
| *G16H 20/40* | (2018.01) |
| *G16H 30/20* | (2018.01) |
| *G16H 50/50* | (2018.01) |

(52) U.S. Cl.
CPC ............. *G06F 3/016* (2013.01); *G09B 23/28* (2013.01); *G09B 23/285* (2013.01); *G16H 30/40* (2018.01); *A61B 34/25* (2016.02); *A61N 1/37205* (2013.01); *G06V 30/224* (2022.01); *G16H 20/40* (2018.01); *G16H 30/20* (2018.01); *G16H 50/50* (2018.01)

(56) References Cited

U.S. PATENT DOCUMENTS

| | | | |
|---|---|---|---|
| 2021/0093385 A1 | 4/2021 | Morvan et al. | |
| 2021/0256875 A1* | 8/2021 | Mosier ................. | B29C 64/393 |
| 2023/0008541 A1* | 1/2023 | Peled ................... | G06T 19/006 |

FOREIGN PATENT DOCUMENTS

| | | | | |
|---|---|---|---|---|
| WO | WO-2019185880 A1 * | 10/2019 | ....... | A61B 17/00234 |
| WO | 2021113370 A1 | 6/2021 | | |

* cited by examiner

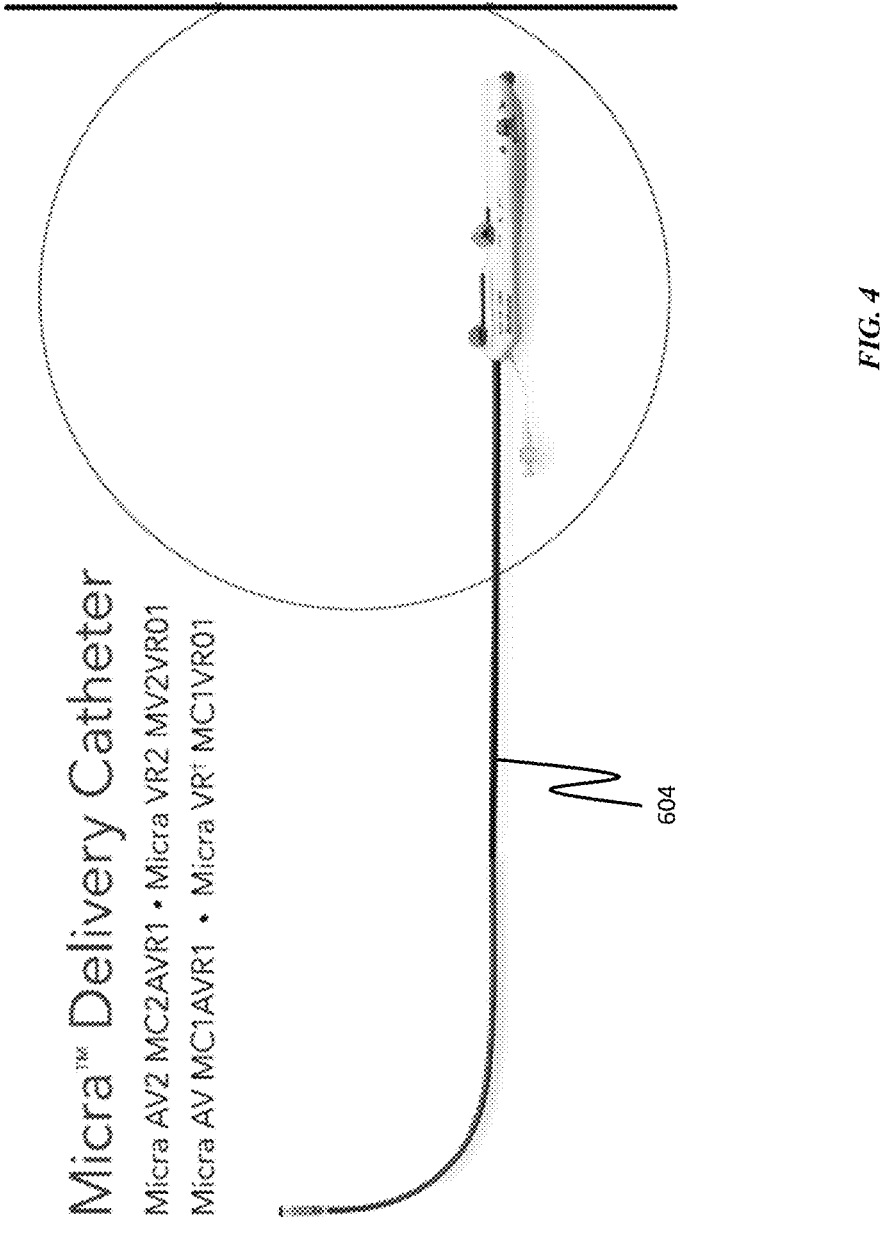
*FIG. 4*

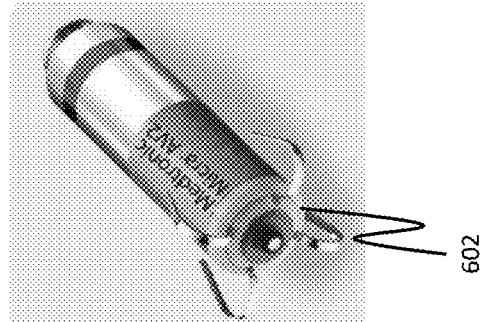
602
*FIG. 6*
600

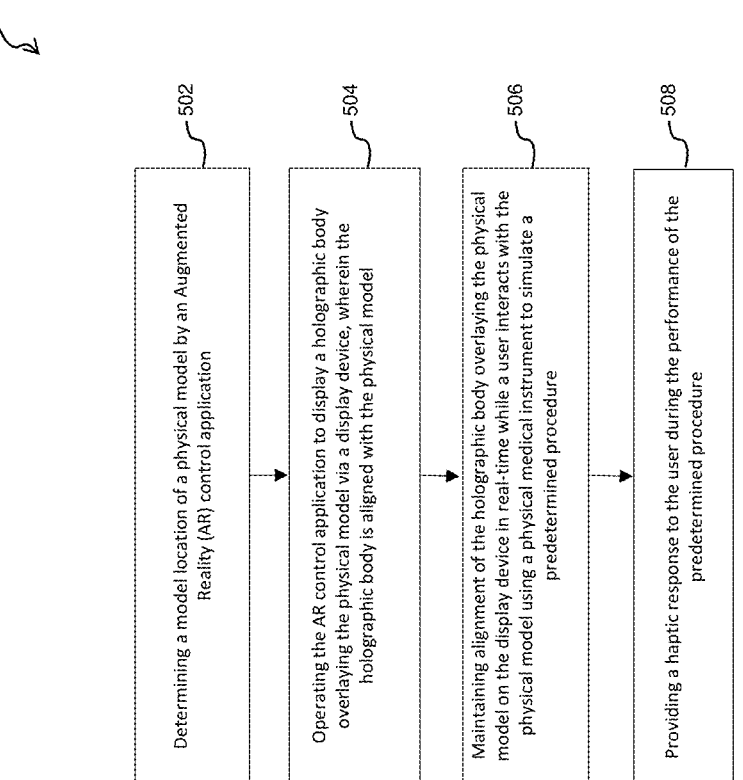

500

502
Determining a model location of a physical model by an Augmented Reality (AR) control application 504
Operating the AR control application to display a holographic body overlaying the physical model via a display device, wherein the holographic body is aligned with the physical model 506
Maintaining alignment of the holographic body overlaying the physical model on the display device in real-time while a user interacts with the physical model using a physical medical instrument to simulate a predetermined procedure 508
Providing a haptic response to the user during the performance of the predetermined procedure

*FIG. 11*

EXTENDED REALITY TRAINING PLATFORM

This application claims priority to Singaporean Patent Application No. 10202250543G, filed on Jul. 22, 2022, and all the benefits accruing therefrom under 35 U.S.C. § 119, the content of which in its entirety is herein incorporated by reference.

FIELD

The present disclosure relates in general to computing technology and, more particularly to the use of computing technology for implementing an Extended Reality (XR) Training Platform.

BACKGROUND

Training regarding new platforms, products and techniques can be expensive in terms of travel time, travel expenses and time away from work. Whether the training is related to technical personnel (such as engineers, technicians), medical personnel (such as Health Care Providers (HCP)), commercial/marketing specialists and/or trainers, to name a few, requiring training can be burdensome on individuals and companies. For example, in health care, requiring training of HCPs can cause not only a training bottleneck for the deployment of new medical platforms, products and techniques, where such medical platforms, products and techniques may include, but are not limited to, minimally invasive cardiac surgery (MICS) technologies from Medtronic.

Additionally, training is further limited by the speed at which the technology provider can reach the HCPs to describe and implement the training, and it may require expensive simulators and/or expensive animal/human cadaver models to provide the real life environment needed to achieve an effective training experience. Once at the training center, in-person training often requires exposure to radiation. To complicate matters more, HCP travel may also require exposure to radiation, which is becoming increasingly subject to higher regulatory scrutiny (e.g., some regulatory agencies do not allow HCPs to train outside of the country where they will be performing the procedures). All of these factors may have a deleterious impact on access to and/or willingness of the personnel to undergo in-person training.

SUMMARY

A method for providing an Extended Reality (XR) training experience is provided and includes determining a model location of a physical model by an augmented reality (AR) control application, operating the AR control application to display a holographic body overlaying the physical model via a display device, wherein the holographic anatomy, body, and/or tools are aligned with the physical model such that a portion of the physical model representing an anatomical structure appears aligned with the holographic anatomy, body, and/or tools in a predetermined anatomical position and orientation, maintaining alignment of the holographic anatomy, body, and/or tools overlaying the physical model on the display device in real-time while a user interacts with the holographic anatomy, body, and/or tools and/or the physical model using a physical input device (hand, wand, stylus, pointer, glove, and/or bodywear) or medical instrument to simulate a predetermined procedure and providing haptic feedback to the user during the predetermined procedure.

A system for providing an Extended Reality (XR) training experience is provided, wherein the system includes a display device, a camera, a memory system and a processing system coupled to the memory system, the processing system configured to execute a plurality of instructions to: capture a view of a physical model by the camera, operate an augmented reality (AR) control application to display a holographic body overlaying the physical model via the display device, wherein the holographic body is aligned with the physical model such that a portion of the physical model representing an anatomical structure appears aligned with the holographic body in a predetermined anatomical position, maintaining alignment of the holographic body overlaying the physical model on the display device in real-time while a user interacts with the physical model using a medical device or simulated tool to simulate performing a predetermined procedure or task and providing feedback to the user during the predetermined procedure.

A computer program product comprising a memory device having computer executable instructions stored thereon, which when executed by one or more processors cause the one or more processors to perform a plurality of operations for implementing a method is provided, wherein the method includes communicating a model location of a physical model to an augmented reality (AR) control application, activating a camera to generate and display images of the physical model on a display device; operating the AR control application to display a holographic body overlaying the physical model to a user via an AR headset worn by the user, wherein the holographic body is aligned with the physical model such that the physical model and its associated structures are precisely anatomically aligned with the holographic body, maintaining alignment of the holographic body overlaying the physical model on the display device while a user interacts with the physical model using a medical device to perform a predetermined procedure, displaying the predetermined procedure on the display device in real-time and providing feedback to the user during the predetermined procedure.

The above features and advantages, and other features and advantages, of the disclosure are readily apparent from the following detailed description when taken in connection with the accompanying drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the aspects of the disclosure are apparent from the following detailed description taken in conjunction with the accompanying drawings in which:

FIG. 4 depicts a medical instrument according to one or more aspects;

FIG. 6 depicts a medical instrument according to one or more aspects;

FIG. 11 depicts an operational block diagram illustrating a method of the invention according to one or more aspects;

Figure 1:
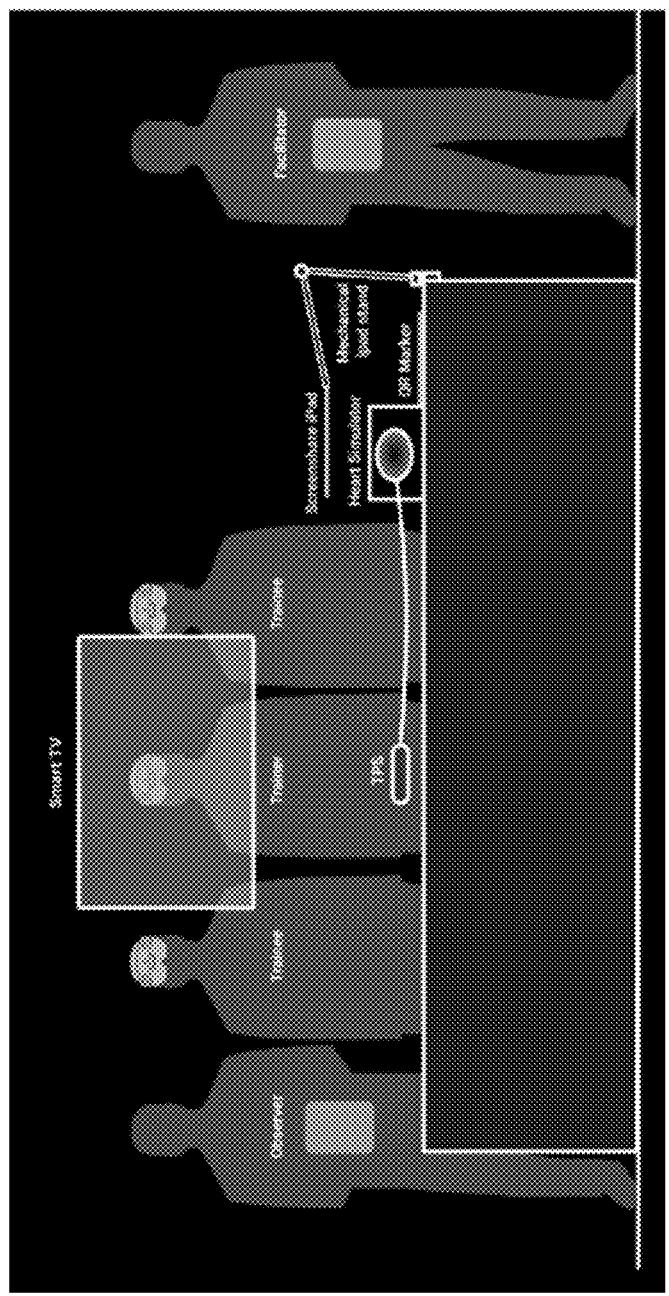
FIG. 1 depicts an Extended Reality Training Platform (XRTP), according to one or more aspects.
Figure 2:
FIG. 2 depicts a holographic image of a body and an internal anatomical structure displayed on a supporting structure according to one or more aspects.
Figure 3:
FIG. 3 depicts a holographic image of a body and an internal anatomical structure displayed on a supporting structure with a medical procedure being performed according to one or more aspects.
Figure 5:
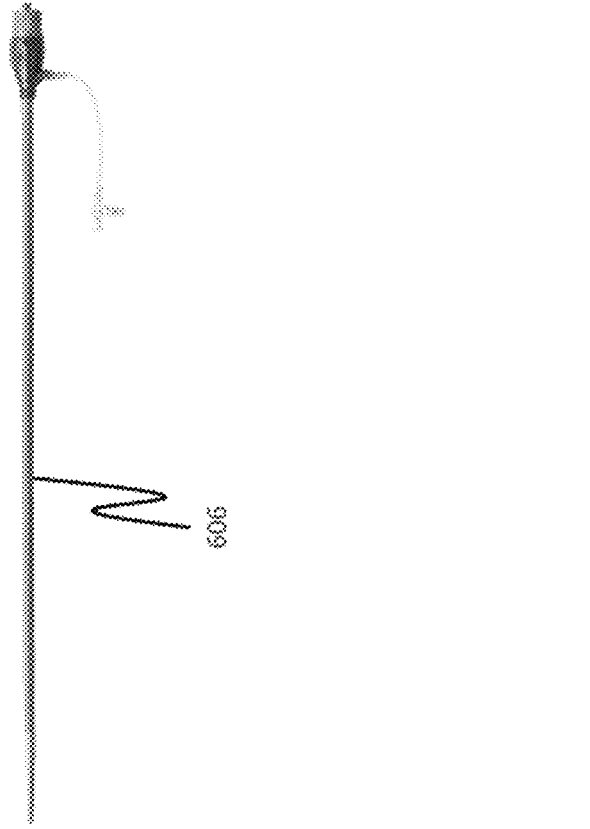
FIG. 5 depicts a medical instrument according to one or more aspects.
Figure 7:
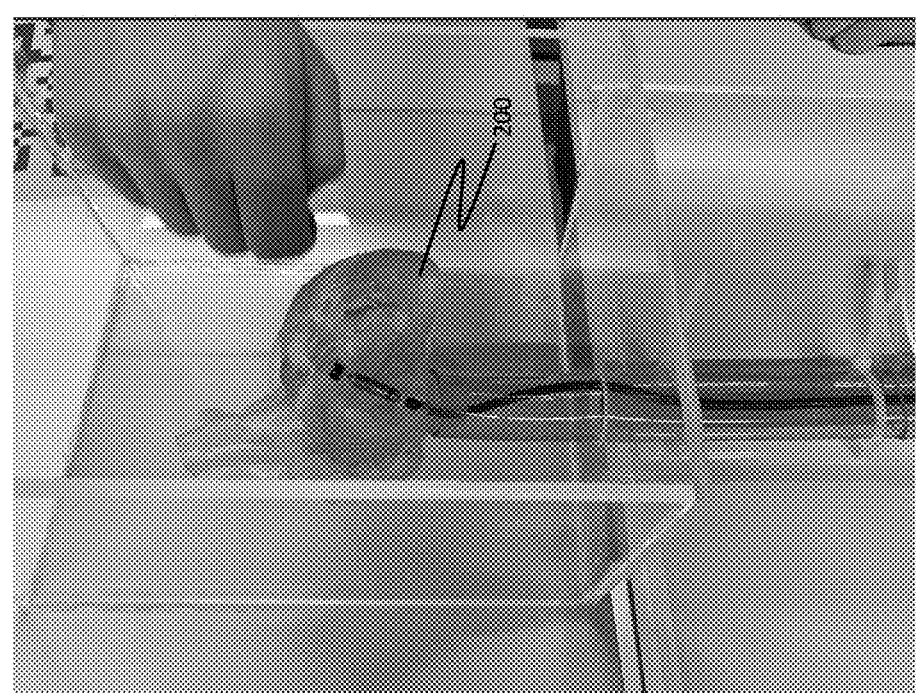
FIG. 7 depicts a physical model according to one or more aspects.
Figure 8:
FIG. 8 depicts a physical model according to one or more aspects.
Figure 9:
FIG. 9 depicts a medical instrument according to one or more aspects.
Figure 10:
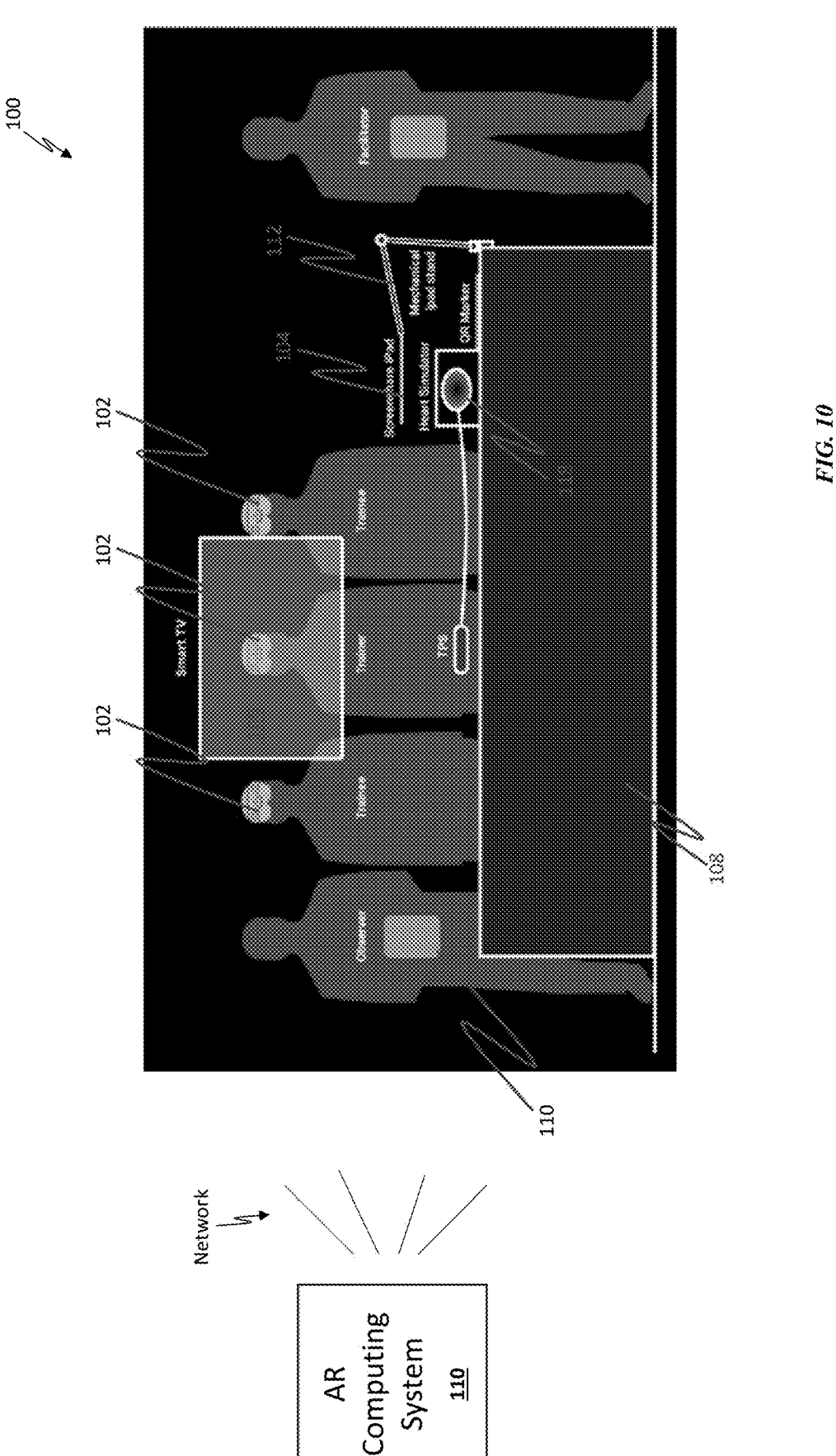
FIG. 10 depicts an Extended Reality Training Platform (XRTP) according to one or more aspects.
Figure 12:
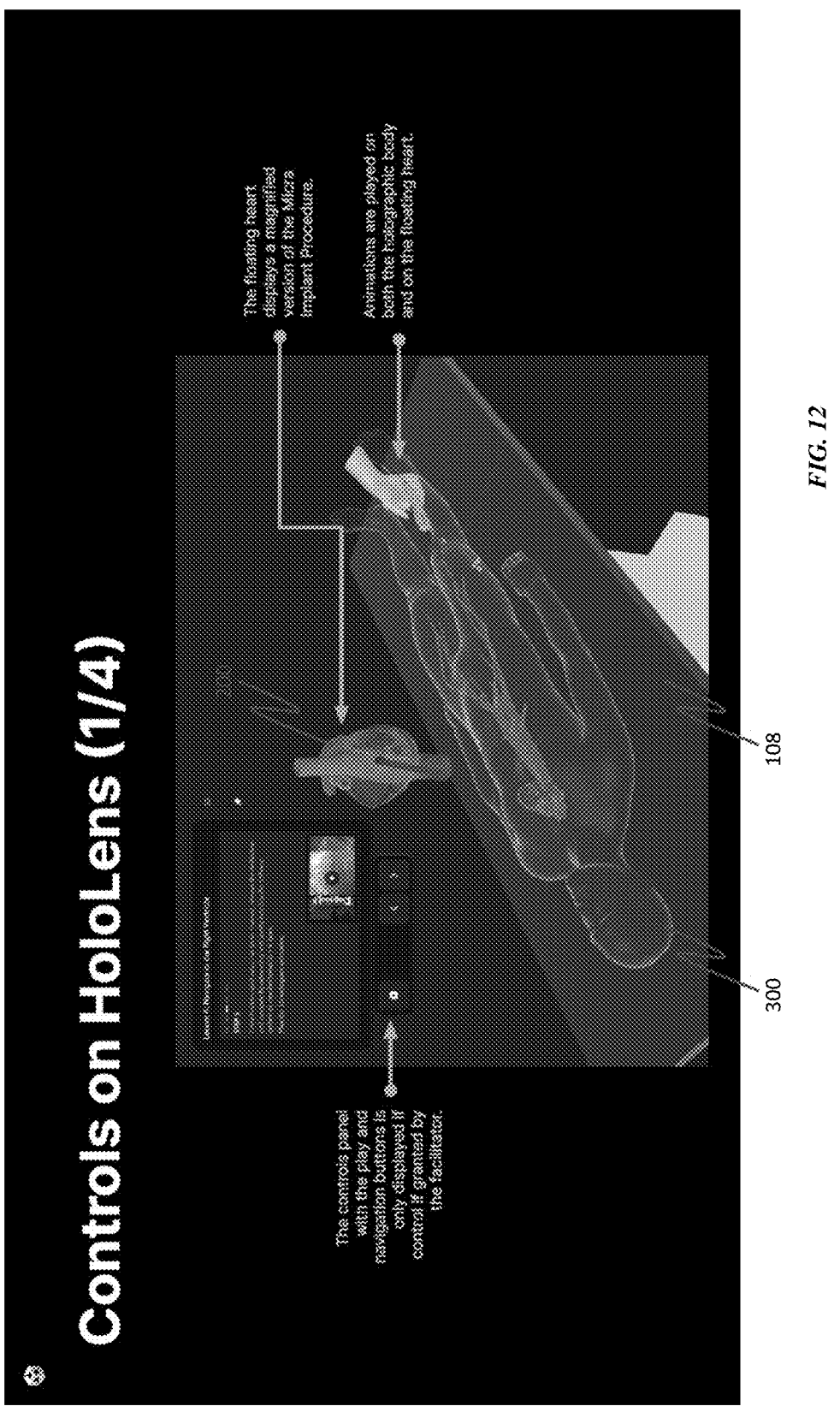
FIG. 12 depicts a visual image that is displayed to a user according to one or more aspects.
Figure 13:
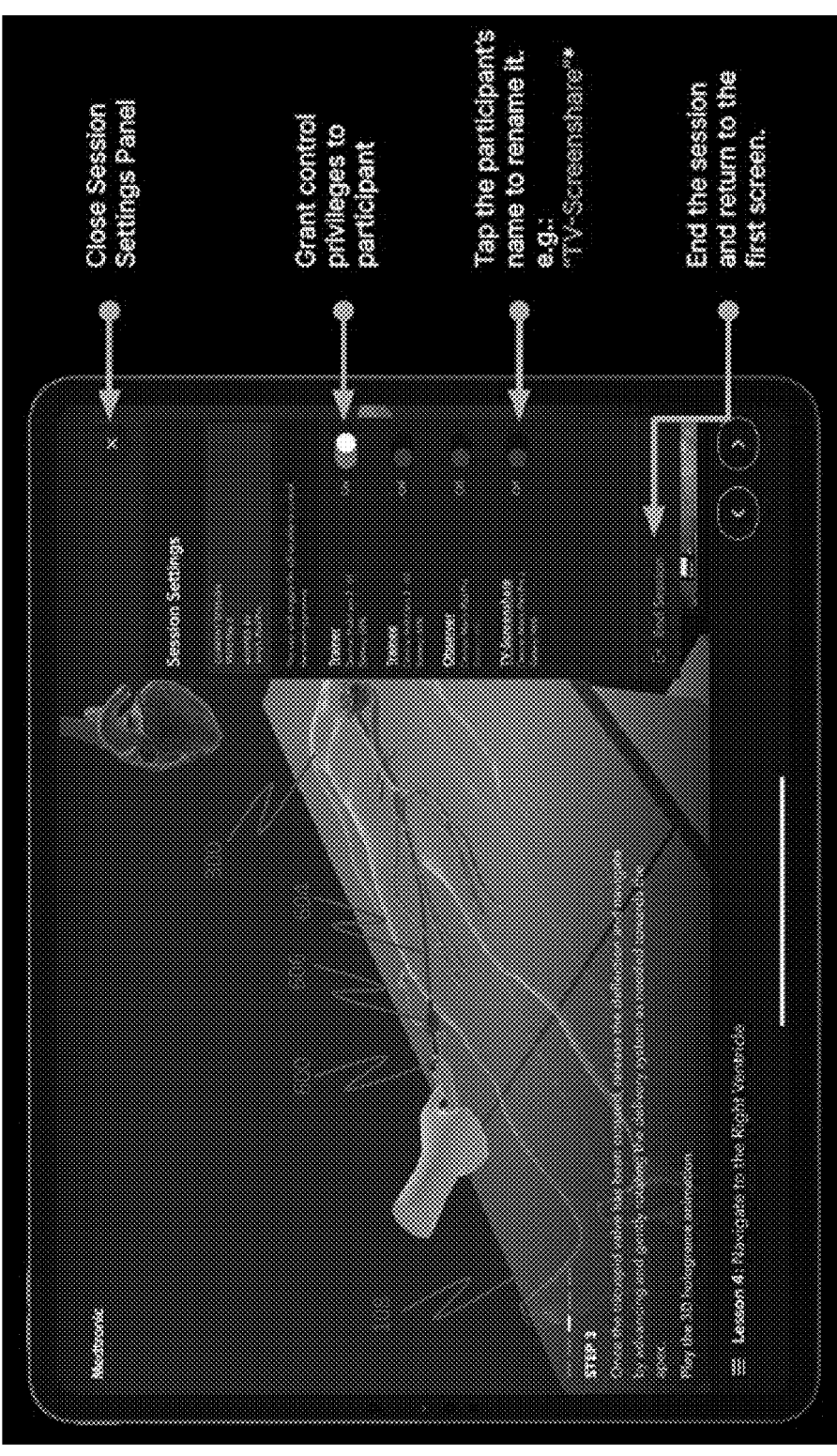
FIG. 13 depicts a visual image that is displayed to a user according to one or more aspects.

The diagrams depicted herein are illustrative. There can be many variations to the diagrams and/or the operations described herein without departing from the spirit of the described aspects. For instance, the actions can be performed in a differing order, or actions can be added, deleted, or modified. Also, the term "coupled" and variations thereof describe having a communications path between two elements and do not imply a direct connection between the elements with no intervening elements/connections between them. All of these variations are considered a part of the specification.

DETAILED DESCRIPTION

Exemplary aspects of the technical solutions described herein include a system and method for training a user via a holographic image overlayed onto a physical model to provide an Extended Reality (XR) experience. It should be appreciated that although the method of the invention is described herein with regards to a medical procedure for placing a Micra pacemaker into the right ventricle of a patient using the Micra® transcatheter pacing system, the method of the invention may be used for any procedure (medical, engineering, etc.) suitable to the desired end purpose that would benefit from an XR experience using a synchronized interaction between a physical model and a holographic overlay.

Referring to the Figures and in accordance with an aspect, the invention includes an Extended Reality Training Platform (XRTP) 100 which includes an AR headset 102, a camera 104, a display device 106, a support structure 108 (hereinafter 'table') and a computing system 110 operating an AR control application to control the visual display interaction between the XRTP 100 and the user. The set up of the XRTP 100 involves placing a physical model of a heart 200 (and all of the associated arteries) onto the table 108 and communicating the location of the physical model 200 on the table 108 to the AR control application. This allows the AR control application to precisely align the holographic image that will be displayed to the user via the AR headset 102 with the physical model 200. For example, once the physical model 200 of the heart/arteries is disposed on the table 108 and the location of the physical model 200 is communicated to the AR control application, the AR control application will display a holographic image of a body 300 which is aligned with the physical model 200. As such, the holographic body 300 is located relative to the physical model 200 so that the physical model 200 of the heart is displayed as being precisely located anatomically in the chest of the holographic body 300. Additionally, the arteries of the physical model 200 are also shown as being precisely located anatomically within the holographic body 300 as they would be in a real life body and presented with overlayed holographic arteries. Thus, when the user puts on the AR headset 102 and views the table 108, the user will see the holographic body 300 displayed on the table 108 to overlay the physical model 200. Thus, the alignment of holographic body 300 with the physical model 200 will provide the user with a real life visual image. If the user walks around the table 108, the user will be shown the combination of the physical model 200 and the holographic body 300 from different viewpoints.

The camera 104 is disposed above (and on the side at various angles) the physical model 200 to view the physical model 200 from above (and from the side at various angles) the physical model 200. The camera 104 will take videos and/or still images of the physical model 200 and the AR control application will display the physical model with the holographic body 200 overlay onto the display device 108 which is located on the opposite side of the table 108 of the user such that the user can view the videos/images as the user is practicing the procedure, similarly to the way the actual procedure is performed. Additionally, the camera 104 is mounted to a camera holder 112 that allows the camera 104 to be rotated about an of arc of about 180° to allow the camera 104 to capture videos/images from either side of the physical model 200 as desired. It should be appreciated that the camera 104 may be configured to mimic an X-Ray device, wherein when the X-Ray images from the camera will be displayed to the user on the display device 106, similarly to the way the actual procedure is performed.

In accordance with an aspect, the invention will be discussed with regards to a medical procedure for placing a Micra pacemaker into the right ventricle of a patient using the Micra® Transcatheter Pacing System (MTPS) 600, wherein the MTPS 600 includes a Micra pacemaker 602, a catheter 604 and an introducer 606. The procedure involves setting up the XRTP 100 by placing the physical model of the heart 200 onto the table 108. The precise location of the heart 200 is communicated to the AR control application to allow the AR control application to align and synchronize the location of the heart 200 with the XRTP 100. It should be appreciated that the location of the heart 200 may be communicated to the AR control application using lidar/ladar/laser, radar, computer vision or marker, such as a QR code (2D or 3D) which is placed at a predetermined location on the table 108 relative to the heart 200. It is contemplated that other ways to communicate the precise location of the heart 200 to the AR control application may also be used, such as via GPS, or by defining a specific location on the table 108, etc.

The camera 104 is mounted to the camera holder 112 and disposed to be located above the heart 200 and looking down onto the heart 200. The camera 104 is activated and configured so that images captured by the camera 104 are displayed on the display device 106. The user puts on and activates the AR headset 102 such that the AR headset 102 is communicated with the AR control application. When the user looks at the table 108 and the heart 200, the AR control application displays a holographic body 300 overlayed onto the table 108 and the heart 200. It should be appreciated that if the user is a new or relatively in experienced physician, the AR control application may display the holographic body 300 as being semi-transparent or 'see through'. This allows the user to see the heart 200 and its associated arteries at their locations in the holographic body 300. This allows the less experienced user to view the heart 200 and its associated arteries during the training procedure to become more familiar with the actual locations for accessing the associated arteries of the heart 200. Accordingly, the user can practice by using both a 'touch' and a visual approach by feeling the arteries and watching the images and animations being displayed on the display device 106 as the procedure progresses.

On the other hand, if the user is an experienced physician, the AR control application may display the holographic body 300 as being opaque, thereby not allowing the user to see the internal anatomy, the physical tools, nor the physical model 200. In this case, the user may use the camera 104 mimicking an X-Ray device that will obtain video images of the heart 200 and its associated arteries and display these images on the display device 106. In this way, the user will be able to practice the procedure using a 'touch' approach while viewing the simulated X-Ray images of the heart 200 and its associated arteries on the display device 106 as the procedure progresses. It should be appreciated that the invention allows for the user to experience practicing the procedure using simulated X-Ray image views without exposing the user (or other individuals located nearby) to radiation.

When the user begins the procedure, the user will assemble the Micra pacemaker 602, the catheter 604 and the introducer 606 of the MTPS 600 (the combination hereinafter referred to as the "Micra") and, wearing the AR headset, locates the femoral artery leading to the heart 200 relative to the holographic body 300. Using the images displayed on the display device 106, the user inserts the Micra into the femoral artery of the holographic body 300. It should be appreciated that the physical model of the heart 200 provides haptic feedback to the user as the procedure progresses. For example, during the procedure, as the Micra traverses the artery, the user may be required to rotate or twist the Micra to navigate through an artery branch. At this point in the procedure, the haptic the physical model of the heart 200 may provide haptic feedback to the user through friction, fluid flow, obstruction, and lack thereof. The combination of haptics and visuals would inform the user that the user needs to rotate or twist the Micra to direct the Micra to the correct branch and to continue the procedure. At this point, the user would continue the procedure until the Micra pacemaker 602 is located and placed with heart 200 and the user would remove the Micra from the physical model of the heart and its associated arteries 200.

It should be appreciated that if the user is a less experienced user, the holographic body 300 may be displayed to the user as a semi-transparent holographic body 300 so that the user can see the heart 200 and its associated arteries through the holographic body 300, as well as on the display device 106. However, if the user is a more experienced user, the holographic body 300 may be displayed to the user as an opaque holographic body 300 and thus the user would not be able to see the physical model 200 and its associated holographic anatomy through the holographic body 300 and would only be able to feel the haptics from the heart 300 and view the images of the progress on the display device 106 and the AR headset 102 (and other display devices, such as tablets, being used with the system). In this case, the user may utilize the camera 104 as an simulated X-Ray device and the simulated X-Ray images would be displayed on the display device 106. The user may orient the camera 104 to take images of the heart 200 and its associated arteries via multiple angles by rotating the camera 104 about the physical simulator (i.e., holographic body 300) as desired. This would give the user different viewpoints of the procedure progress.

In accordance with an aspect and referring to FIG. 11, a method 500 for providing an Augmented Reality (AR) training experience using a medical device, a physical model and a holographic overlay is provided and includes determining a model location of a physical model by an augmented reality (AR) control application, as shown in operational block 502. As discussed above, in one aspect the medical device may be a Micra® Transcatheter Pacing System (MTPS) 600 having a Micra pacemaker 602, a catheter 604 and an introducer 606 and the physical model may be a model of a heart 200 and its associated arteries. However, it other aspects the medical device may be any medical device and the physical model may be a model of any anatomical body part that will be used for training a user on a predetermined procedure.

In one aspect, this may be accomplished by associating a QR code (2D or 3D) with the model location. However, it is contemplated that the model location may be communicated to the AR control application using any method suitable to the desired end purpose, such as GPS sensing device, ladar, computer vision, designating a predefined location on the support structure 108, etc. The camera is activated to cause the camera to generate images of the physical model and display those images on the display device. The camera may be mounted in the camera holder 122 to be located above the physical model 200 to take images of the physical model 200 during the predefined procedure. It is contemplated that the camera is movable about the table to take images of the physical model from different angles. Additionally, it is contemplated that the camera is configurable to take and display simulated X-Ray images of the physical model 200 from different angles.

The method further includes operating the AR control application to display a holographic body overlaying the physical model via a display device, wherein the holographic body is aligned with the physical model such that a portion of the physical model representing an anatomical structure appears aligned with the holographic body in a predetermined anatomical position, as shown in operational block 504. It should be appreciated that communicating the precise model location to the AR control application allows the AR control application to precisely display the holographic body relative to the physical model so that the physical model is anatomically positioned 'within' the holographic body. For example, if the physical model is a heart and its associated arteries, then the AR control application will locate the holographic body such that the elements of the physical model are located in the correct anatomical locations (i.e., the heart in the thoracic cavity and the femoral artery in the femoral triangle). Moreover, it is contemplated that the AR control application may adjust the holographic body to have a transparency that ranges from transparent to opaque to allow users having a range of experience to practice procedures.

The method 500 further includes maintaining alignment of the holographic body overlaying the physical model on the display device in real-time while a user interacts with the physical model using a physical medical instrument to simulate a predetermined procedure, as shown in operational block 506. In one aspect, this may be accomplished by using the introducer 606 to position the catheter 604 and the Micra pacemaker 602 into the femoral artery of the physical model 200 and operate the catheter 604 to traverse the femoral artery until the Micra pacemaker is disposed in the ventricle of the heart 200. As the procedure is being performed, the camera 104 will be obtaining images of the procedure and displaying the images in real-time to the user via the display device 106 to provide a real-world simulation of the procedure to the user. The method 500 further includes providing haptic feedback to the user during the predetermined procedure, as shown in operational block 508. It should be appreciated that at least one of the physical model 200 and the AR control application may be configured to provide haptic feedback to the user during the performance of the predetermined procedure.

It should be appreciated that aligning the augmented reality hologram with the physical model 200 may be executed though computer vision and/or markers such as QR codes. The location and orientation of the physical model 200 may be identified through these methods and the Augmented Reality (AR) is then overlayed accordingly. Simulating x-ray vision may be executed digitally and via the camera 104. A digital x-ray is generated based on the augmented reality view. The digital camera 104 is used to capture a view of the physical model 200. These two views can be overlayed if desired. The x-ray views can be displayed on the display device 106 and/or generated in augmented reality and displayed on the AR headset 102. The camera 104 can be rotated around the simulator as an x-ray would. A digitally generated x-ray view can also be controlled to rotate around the augmented reality model in the same way an x-ray would.

Moreover, the physical model 200 and the holographic body 300 can be displayed on any viewing device including tablets and goggles. The augmented reality model can be displayed semi-transparently such that the body and internal anatomy are visible, the physical model 200 is visible, and any handheld tools are visible. The augmented reality model 300 can be displayed opaquely such that only the holographic body 300 and internal anatomy are visible, obscuring the physical model 200 or the augmented reality model 300 can be displayed opaquely such that only the holographic body 300 is visible, without internal anatomy, obscuring the physical model 200 and forcing the user to utilize the x-ray (generated or captured via camera) to see their actions and tool location. The system is operational without any physical models 200. Areas of interest or anatomy can be displayed outside the augmented reality body 300 for easier, enlarged viewing.

Additionally, although the invention is disclosed herein as being implemented using a AR headset 102, it is contemplated that any device suitable to the desired end purpose may be used to implement the invention, such as a laptop computer, a tablet, a PDA, a cell phone, etc.

The processing shown in FIG. 11 is not intended to indicate that the operations are to be executed in any particular order or that all of the operations shown in FIG. 11 are to be included in every case. Additionally, the processing shown in FIG. 11 can include any suitable number of additional operations.

Figure 14:
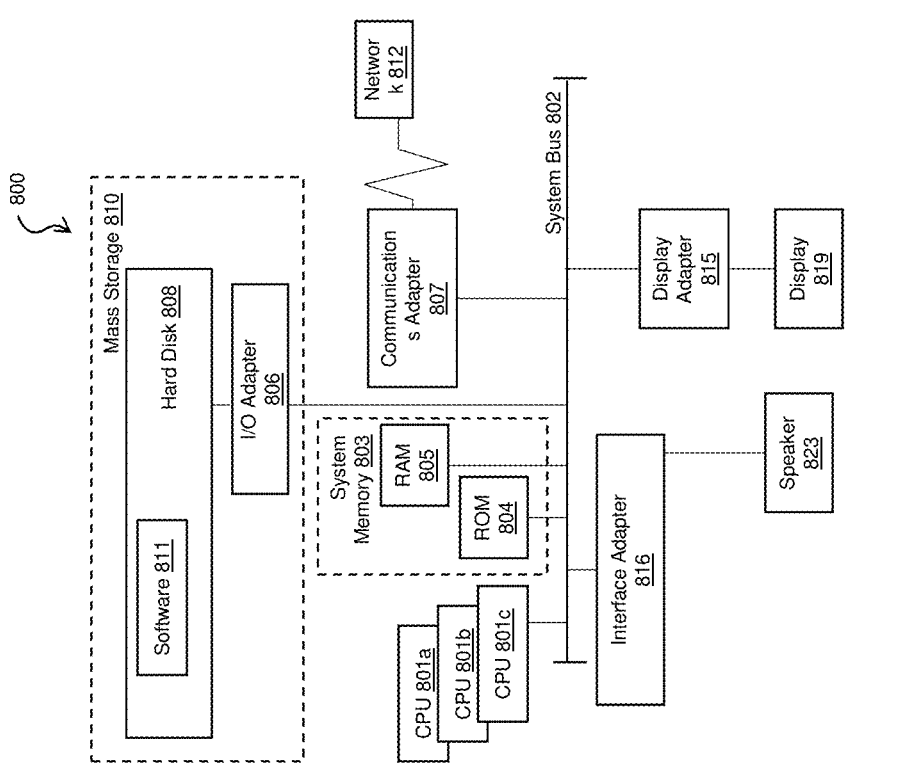
FIG. 14 depicts a block diagram of a computer system, according to one or more aspects.

Turning now to FIG. 14, a computer system 800 is generally shown in accordance with an aspect. The computer system 800 can be an electronic computer framework comprising and/or employing any number and combination of computing devices and networks utilizing various communication technologies, as described herein. The computer system 800 can be easily scalable, extensible, and modular, with the ability to change to different services or reconfigure some features independently of others. The computer system 800 may be, for example, a server, desktop computer, laptop computer, tablet computer, or smartphone. In some examples, computer system 800 may be a cloud computing node. Computer system 800 may be described in the general context of computer-executable instructions, such as program modules, being executed by a computer system. Generally, program modules may include routines, programs, objects, components, logic, data structures, and so on that perform particular tasks or implement particular abstract data types. Computer system 800 may be practiced in distributed cloud computing environments where tasks are performed by remote processing devices that are linked through a communications network. In a distributed cloud computing environment, program modules may be located in both local and remote computer system storage media, including memory storage devices.

As shown in FIG. 14, the computer system 800 has one or more central processing units (CPU(s)) 801*a*, 801*b*, 801*c*, etc. (collectively or generically referred to as processor(s) 801). The processors 801 can be a single-core processor, multi-core processor, computing cluster, or any number of other configurations. The processors 801 can be any type of circuitry capable of executing instructions. The processors 801, also referred to as processing circuits, are coupled via a system bus 802 to a system memory 803 and various other components. The system memory 803 can include one or more memory devices, such as read-only memory (ROM) 804 and a random-access memory (RAM) 805. The ROM 804 is coupled to the system bus 802 and may include a basic input/output system (BIOS), which controls certain basic functions of the computer system 800. The RAM is read-write memory coupled to the system bus 802 for use by the processors 801. The system memory 803 provides temporary memory space for operations of said instructions during operation. The system memory 803 can include random access memory (RAM), read-only memory, flash memory, or any other suitable memory systems.

The computer system 800 comprises an input/output (I/O) adapter 806 and a communications adapter 807 coupled to the system bus 802. The I/O adapter 806 may be a small computer system interface (SCSI) adapter that communicates with a hard disk 808 and/or any other similar component. The I/O adapter 806 and the hard disk 808 are collectively referred to herein as a mass storage 810.

Software 811 for execution on the computer system 800 may be stored in the mass storage 810. The mass storage 810 is an example of a tangible storage medium readable by the processors 801, where the software 811 is stored as instructions for execution by the processors 801 to cause the computer system 800 to operate, such as is described hereinbelow with respect to the various Figures. Examples of computer program product and the execution of such instruction is discussed herein in more detail. The communications adapter 807 interconnects the system bus 802 with a network 812, which may be an outside network, enabling the computer system 800 to communicate with other such systems. In one aspect, a portion of the system memory 803 and the mass storage 810 collectively store an operating system, which may be any appropriate operating system to coordinate the functions of the various components shown in FIG. 14.

Additional input/output devices are shown as connected to the system bus 802 via a display adapter 815 and an interface adapter 816. In one aspect, the adapters 806, 807, 815, and 816 may be connected to one or more I/O buses that are connected to the system bus 802 via an intermediate bus bridge (not shown). A display 819 (e.g., a screen or a display monitor) is connected to the system bus 802 by a display adapter 815, which may include a graphics controller to improve the performance of graphics-intensive applications and a video controller. A keyboard, a mouse, a touchscreen, one or more buttons, a speaker, etc., can be interconnected to the system bus 802 via the interface adapter 816, which may include, for example, a Super I/O chip integrating multiple device adapters into a single integrated circuit. Suitable I/O buses for connecting peripheral devices such as hard disk controllers, network adapters, and graphics adapters typically include common protocols, such as the Peripheral Component Interconnect (PCI). Thus, as configured in FIG. 14, the computer system 800 includes processing capability in the form of the processors 801, and storage capability including the system memory 803 and the mass storage 810, input means such as the buttons, touchscreen, and output capability including the speaker 823 and the display 819.

In some aspects, the communications adapter 807 can transmit data using any suitable interface or protocol, such as the internet small computer system interface, among others. The network 812 may be a cellular network, a radio network, a wide area network (WAN), a local area network (LAN), or the Internet, among others. An external computing device may connect to the computer system 800 through the network 812. In some examples, an external computing device may be an external web server or a cloud computing node.

It is to be understood that the block diagram of FIG. 14 is not intended to indicate that the computer system 800 is to include all of the components shown in FIG. 14. Rather, the computer system 800 can include any appropriate fewer or additional components not illustrated in FIG. 14 (e.g., additional memory components, embedded controllers, modules, additional network interfaces, etc.). Further, the aspects described herein with respect to computer system 800 may be implemented with any appropriate logic, wherein the logic, as referred to herein, can include any suitable hardware (e.g., a processor, an embedded controller, or an application-specific integrated circuit, among others), software (e.g., an application, among others), firmware, or any suitable combination of hardware, software, and firmware, in various aspects. Various aspects can be combined to include two or more of the aspects described herein.

Aspects disclosed herein may be a system, a method, and/or a computer program product at any possible technical detail level of integration. The computer program product may include a computer-readable storage medium (or media) having computer-readable program instructions thereon for causing a processor to carry out various aspects.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device, such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network, and/or a wireless network. The network may comprise copper transmission cables, optical transmission fibers, wireless transmission, routers, firewalls, switches, gateway computers, and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out operations of the present disclosure may be assembler instructions, instruction-set-architecture (ISA) instructions, machine instructions, machine-dependent instructions, microcode, firmware instructions, state-setting data, configuration data for integrated circuitry, or either source-code or object code written in any combination of one or more programming languages, including an object-oriented programming language, such as Smalltalk, C++, high-level languages such as Python, or the like, and procedural programming languages, such as the "C" programming language or similar programming languages. The computer-readable program instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some aspects, electronic circuitry including, for example, programmable logic circuitry, field-programmable gate arrays (FPGA), or programmable logic arrays (PLA) may execute the computer-readable program instruction by utilizing state information of the computer-readable program instructions to personalize the electronic circuitry, in order to perform aspects of the present disclosure.

Aspects are described herein with reference to flowchart illustrations and/or block diagrams of methods, apparatus (systems), and computer program products according to aspects of the disclosure. It will be understood that each block of the flowchart illustrations and/or block diagrams, and combinations of blocks in the flowchart illustrations and/or block diagrams, can be implemented by computer-readable program instructions.

These computer-readable program instructions may be provided to a processor of a computer system, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flow-chart and/or block diagram block or blocks.

The computer-readable program instructions may also be loaded onto a computer, other programmable data processing apparatus, or other device to cause a series of operational steps to be performed on the computer, other programmable apparatus or other devices to produce a computer-imple-mented process, such that the instructions which execute on the computer, other programmable apparatus, or other device implement the functions/acts specified in the flow-chart and/or block diagram block or blocks.

The flowchart and block diagrams in the Figures illustrate the architecture, functionality, and operation of possible implementations of systems, methods, and computer pro-gram products according to various aspects. In this regard, each block in the flowchart or block diagrams may represent a module, segment, or portion of instructions, which com-prises one or more executable instructions for implementing the specified logical function(s). In some alternative imple-mentations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various aspects have been pre-sented for purposes of illustration but are not intended to be exhaustive or limited to the aspects disclosed. Many modi-fications and variations will be apparent to those of ordinary skill in the art without departing from the scope and spirit of the described aspects. The terminology used herein was chosen to best explain the principles of the aspects, the practical application or technical improvement over tech-nologies found in the marketplace, or to enable others of ordinary skill in the art to understand the aspects described herein.

Various aspects are described herein with reference to the related drawings. Alternative aspects can be devised without departing from the scope of this disclosure. Various connec-tions and positional relationships (e.g., over, below, adja-cent, etc.) are set forth between elements in the following description and in the drawings. These connections and/or positional relationships, unless specified otherwise, can be direct or indirect, and the present disclosure is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains," or "containing," or any other variation thereof are intended to cover a non-exclusive inclusion. For example, a composi-tion, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any aspect or design described herein as "exemplary" is not necessarily to be construed as preferred or advantageous over other aspects or designs. The terms "at least one" and "one or more" may be understood to include any integer number greater than or equal to one, i.e., one, two, three, four, etc. The terms "a plurality" may be understood to include any integer number greater than or equal to two, i.e., two, three, four, five, etc. The term "connection" may include both an indirect "connection" and a direct "connection."

The terms "about," "substantially," "approximately," and variations thereof are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known sys-tem and/or process details.

It should be understood that various aspects, and/or parts of the aspects, disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the tech-niques of this disclosure may be performed by a combina-tion of units or modules associated with, for example, a medical device.

In one or more examples, the described techniques may be implemented in hardware, software, firmware, or any com-bination thereof. If implemented in software, the functions may be stored as one or more instructions or code on a computer-readable medium and executed by a hardware-based processing unit. Computer-readable media may include non-transitory computer-readable media, which cor-responds to a tangible medium, such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), graphics processing units (GPUs), microprocessors, appli-cation-specific integrated circuits (ASICs), field program-mable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A method comprising:

determining a model location of a physical model by an augmented reality (AR) control application;

operating the AR control application to select for display a transparent image or an opaque image of a holographic body overlaying the physical model via a display device based on an experience level of a user of the AR control application, wherein the holographic body is aligned with the physical model such that a portion of the physical model representing an anatomical structure appears aligned with the holographic body in a predetermined anatomical position;

maintaining alignment of the holographic body overlaying the physical model on the display device in real-time while the user interacts with the physical model using a physical medical instrument to simulate a predetermined procedure; and providing haptic feedback to the user during the predetermined procedure.

2. The method of claim 1, wherein determining the model location comprises capturing an image of a quick response (QR) code at a predetermined position proximate to the physical model as an alignment indicator.

3. The method of claim 1, wherein determining the model location comprises at least one of locating the physical model in a predefined location on a support structure, and using a GPS sensing device.

4. The method of claim 1, further comprising activating a camera to simulate an X-Ray device to generate simulated X-Ray images and display the simulated X-Ray images on the display device.

5. The method of claim 1, wherein operating includes operating the AR control application to allow multiple users to view the predetermined procedure using at least one of, an AR headset, and a tablet display device.

6. The method of claim 1, wherein the predetermined procedure comprises interacting with a pacemaker, a catheter and an introducer, and the anatomical structure comprises a heart and its associated arteries include a femoral artery.

7. The method of claim 6, wherein the predetermined procedure comprises inserting the pacemaker through a femoral artery to a heart of the physical model via the introducer.

8. The method of claim 7, wherein the predetermined procedure comprises traversing the femoral artery until the pacemaker is disposed within a ventricle of the heart.

9. The method of claim 1, wherein at least one of, the physical model is configured to provide haptic feedback to the user, and the AR control application is configured to provide haptic feedback to the user.

10. A system comprising:

a display device;

a camera;

a memory system; and a processing system coupled to the memory system, the processing system configured to execute a plurality of instructions to:

capture a view of a physical model by the camera;

operate an augmented reality (AR) control application to select for display a transparent image or an opaque image of a holographic body overlaying the physical model via the display device based on an experience level of a user of the system, wherein the holographic body is aligned with the physical model such that a portion of the physical model representing an anatomical structure appears aligned with the holographic body in a predetermined anatomical position;

maintain alignment of the holographic body overlaying the physical model on the display device in real-time while the user interacts with the physical model using a medical device to simulate performing a predetermined procedure; and provide feedback to the user during the predetermined procedure.

11. The system of claim 10, wherein the processing system is configured to execute a plurality of instructions to determine a model location of the physical model on a support structure by capturing an image of a quick response (QR) code at a predetermined position proximate to the physical model as an alignment indicator.

12. The system of claim 10, wherein the processing system is configured to execute a plurality of instructions to determine a model location of the physical model on a support structure via, at least one of locating the physical model in a predefined location on the support structure, and using a GPS sensing device.

13. The system of claim 10, wherein the processing system is configured to execute a plurality of instructions to simulate an X-Ray device to generate simulated X-Ray images and display the simulated X-Ray images on the display device.

14. The system of claim 10, wherein operation of the AR control application comprises supporting multiple users to view the predetermined procedure using at least one of, an AR headset, and a tablet display device.

15. The system of claim 10, wherein at least one of, the physical model is configured to provide haptic feedback to the user, and the AR control application is configured to provide haptic feedback to the user.

16. A computer program product comprising a memory device having computer executable instructions stored thereon, which when executed by one or more processors cause the one or more processors to perform a plurality of operations for implementing a method comprising:

communicating a model location of a physical model to an augmented reality (AR) control application;

activating a camera to generate and display images of the physical model on a display device;

operating the AR control application to select for display a transparent image or an opaque image of a holographic body overlaying the physical model to a user via an AR headset worn by the user based on an experience level of a user of the AR control application, wherein the holographic body is aligned with the physical model such that the physical model and its associated structures are precisely anatomically aligned with the holographic body;

maintaining alignment of the holographic body overlaying the physical model on the display device while a user interacts with the physical model using a medical device to perform a predetermined procedure;

displaying the predetermined procedure on the display device in real-time; and providing feedback to the user during the predetermined procedure.

17. The computer program product of claim 16, wherein the plurality of operations further include, communicating the model location using a QR code, wherein the QR code is read and communicated to the AR control application by the AR headset, operating the AR control application to allow multiple users to view the predetermined procedure using at least one of, another AR headset, and a tablet display device.

\* \* \* \* \*